United States Patent [19]

McLaughlin

[11] 4,425,204

[45] Jan. 10, 1984

[54] RAPID METHOD FOR THE ETCHING AND CLEANING OF DENTAL CASTING METALS

[76] Inventor: Gerald McLaughlin, 550 Rte. 25A, Rocky Point, N.Y. 11778

[21] Appl. No.: 420,014

[22] Filed: Sep. 20, 1982

[51] Int. Cl.³ .................... C25F 1/04; C25F 3/02; C25F 7/00
[52] U.S. Cl. .................... 204/129.7; 204/129.75; 204/144.5; 204/222; 204/273
[58] Field of Search .............. 204/141.5, 144.5, 129.7, 204/129.75, 222, 273

[56] References Cited

U.S. PATENT DOCUMENTS

| | | | |
|---|---|---|---|
| 2,482,486 | 9/1949 | Irish | 204/141.5 |
| 2,702,260 | 2/1955 | Massa | 204/273 |
| 2,780,594 | 2/1957 | Dailey | 204/141.5 |
| 2,861,932 | 11/1958 | Pohl | 204/129.7 |
| 2,888,939 | 6/1959 | Nitsche | 204/222 |
| 3,066,084 | 11/1962 | Osterman, Jr. | 204/129.7 |
| 3,411,999 | 11/1968 | Weinberg | 204/129.7 |
| 3,497,445 | 2/1970 | Berglund | 204/141.5 |

OTHER PUBLICATIONS

Metal Finishing, vol. 77, No. 13 Jan. 1979 p. 128.

*Primary Examiner*—T. M. Tufariello

[57] ABSTRACT

A process for rapidly etching and cleaning dental metal castings which result in a saving of time to the dentists of as much as 1000 percent as compared to prior art methods. A bath combining both etchant and cleaners is applied to the dental casting and agitated ultrasonically. A depleting current is simultaneously passed through the casting and the bath to further increase the rate at which the cleaning and etching process may progress. This procedure results in a combined cleaning and etching process which is faster than was possible previously for either process alone.

8 Claims, 2 Drawing Figures

RAPID METHOD FOR THE ETCHING AND CLEANING OF DENTAL CASTING METALS

FIELD

The present invention relates to the etching and cleaning of metals and, more particularly, to such etching and cleaning processes as applied to dental restorations.

BACKGROUND

Modern dental practice now applies precious and nonprecious metal castings in the mouth for restoration purposes by bonding these castings directly to the teeth. In some cases, such castings, covered with special plastic or porcelain coatings are installed to replace missing teeth, in which case they are bonded to other existing teeth. The bonding is carried out by applying epoxies or other glues that are designed to withstand the eroding action of saliva as well as provide the strength necessary for the teeth to function normally. However, in order for the epoxy to adhere to the castings, it is necessary to roughen the surface of the metal where it is to be bonded to provide a surface to which the epoxy may adhere. This process is generally accomplished by placing the casting into an etching solution where the etching process proceeds at an uneven rate over the surface to produce the desired rough surface.

Unfortunately, the etching solution also darkens the surface of the metal and in many cases leaves a residue which must be cleaned before applying the bonding material. Cleaning is accomplished by placing the metal in a separate cleaning solution for a sufficient period to remove the discoloration and residue, after which the metal is ready for bonding.

This process is shown in greater detail in FIG. 2. In this Figure, the etching apparatus is shown to comprise a first cleaning tank 201 having a cleaning solution 202, an agitator blade 209 supported by shaft 208 from motor 207, a plating electrode 206, a second plating electrode 203 having a head 205 which holds the casting piece 204. FIG. 2 also shows the cleaning apparatus to comprise a separate tank 210 containing a cleaning solution 215, a support rod 211 with a head 212 holding the dental casting piece 213 and an ultrasonic vibrator 214.

The etching process is usually carried out by placing the casting metal 204 in a solution of either sulfuric or nitric acid, passing a current through the electrode 203, the solution 202 and electrode 206 at a density which is typically 0.4 to 0.5 amperes per centimeter of the castings surface area. Current is passed in a direction which is opposite that used for plating. This process might be referred to as electrical deplating. The motor 207 operates the shaft 208 to drive the impeller 209 in order to keep a fresh supply of acid continually circulating about the surface of the casting metal. The time for this process is usually 2 to 5 minutes.

The cleaning operation is usually carried out as shown to the right in FIG. 2. The casting metal 213 is immersed in a cleaning solution 215 such as hydrochloric acid for a period of 10 minutes; however, if the casting metal is not sufficiently cleaned in this period, it is returned to the bath for another ten minute period. The head 212 of support rod 211 holds the casting metal 213 within the solution. The tank 210 holds the cleaning solution and also contains an ultrasonic vibrator 214 which operates to rapidly agitate the solution as well as vibrate the casting metal, accelerating the cleaning action.

Although there are a number of currently used cleaning and etching systems available, as evidenced by U.S. Pat. Nos. 2,616,820, 2,861,932 and 3,411,999, none appear applicable to provide the desired rough etching or speed the operations.

U.S. Pat. No. 2,616,820 is primarily concerned with cleaning using ultrasonic vibrations. U.S. Pat. No. 2,861,932 is directed at a method of treating semiconductors and primarily to etching the semiconductors using electric current in a vibrating bath at a reduced temperature. However, a cleaning operation is not carried out simultaneously with the etching operation in this invention, nor is there any indication of time reductions of the order necessary to provide an efficient dental operation.

U.S. Pat. No. 3,411,999 is directed to a method of etching metals uniformly along a surface. In this process, a current is passed through the metal to be etched. The metal is immersed in an etchant bath and the entire bath is vabrated. The vibration is intended to obtain a uniform surface rather than an uneven surface as is desired for a dental casting metal.

Generally, the prior art processes are designed to either reduce bulk or polish the metal, but none are directed at roughening the metal's surface with specific pitting depth, width and distribution density, all of which are required for satisfactory bonding with current available bonding agents.

The current method typically used by a dentist was so time consuming that it was impractical to etch and clean the metal and install the casting in one visit. This would result in an additional visit by the patient. The time needed to prepare a treatment room combined with the time for cleanup after a visit adds appreciable unproductive time to the procedure.

For example, the prior art total time for etching, bath transfer and cleaning amounted to 26 minutes, preventing installation of the casting in the usual one-half hour appointment period. The time lost in setup at the next visit is typically 9 minutes and includes cleanup of the room, greeting, and settling the patient in the chair. A process for producing the etched and cleaned metal in under 100 seconds is a serious need for the dental profession. The improvement in efficiency could be well over 1000 percent.

SUMMARY

It is an object of the present invention to reduce the time consumed in preparing a dental casting metal from 26 minutes down to 100 seconds.

It is an object of the present invention to combine both cleaning and etching process in a single, more rapidly carried out process.

It is an object of the present invention to use ultrasonic vibrations for the etching and cleaning processes which are carried out simultaneously.

In the present invention the total time for etching and cleaning is reduced from a time as long as 26 minute period down to less than 100 seconds. This saving in time eliminates the need for a second visit and it permits the dentist to at least double his output. In the present invention both the cleaning and etching fluids are combined in a single bath which is agitated by ultrasonic vibrations. A low value of deplating current is passed through the casting metal during the combined cleaning and etching operation to further accelerate the process.

This process not only is faster than the combined total of the prior art cleaning and etching processes, but is faster than either one of them taken individually.

DETAILED DESCRIPTION OF THE INVENTION

Figure 1:
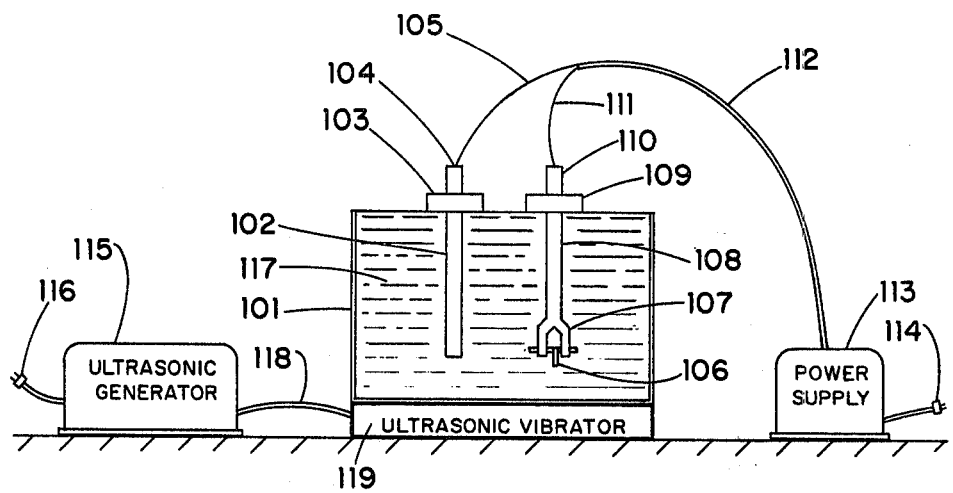
FIG. 1 is a diagram showing a cross section view of the apparatus used in the present invention.
Figure 2:
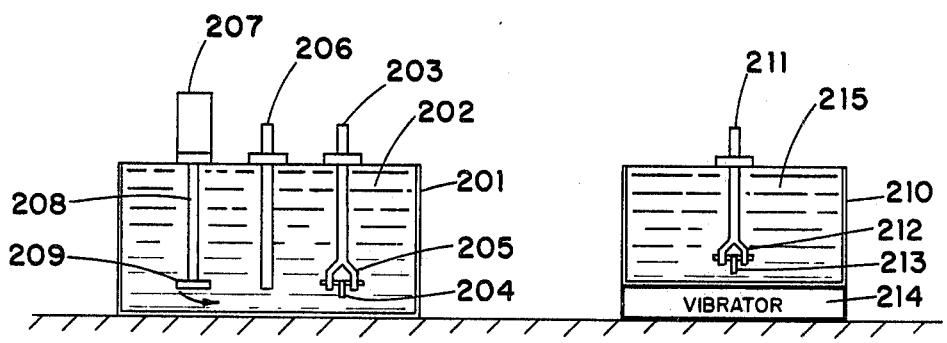
FIG. 2 is a diagram showing a cross sectional view of the apparatus used in prior art systems for cleaning and etching dental castings.

The diagram shown in FIG. 1 illustrates the operation of the present invention. This Figure includes a solution tank 101 containing a solution 117, electroplating rod 102, with a support 103 and contact 105, a second electroplating rod 108 with a support 109 and a contact 110, a head 107, which secures the dental casting metal 106, a power supply 113 with an AC supply input 114, an output line 112 that divides into separate positive and negative lines 111 and 105 which are connected to contacts 110 and 104, respectively, of the electroplating rods. The dental casting may be alternatively secured to the second electroplating rod with wax, provided electrical contact between the two is maintained. FIG. 1 also shows an ultrasonic generator 115 receiving power from line 116 and supplying ultrasonic signals via line 118 to an ultrasonic vibrator 119 located in the tank 101.

In the operation of this apparatus, the ultrasonic generator 115 supplies power to the ultrasonic vibrator 119 which sends ultrasonic waves through the solution 117 causing the solution to be agitated which, in turn, vibrates the dental casting metal 107. The solution 117 contains a mixture of both cleaning and etching solution, such as a mixture of hydrochloric and sulfuric acid. The bath 117 is designed to perform both cleaning and etching simultaneously. This operation is aided by the ultrasonic vibrator and the deplating action carried out by the current from the power supply passing through the electrodes, casting metal and the solution. The current must be maintained at a low value generally less than 0.8 amperes per square centimeter in order to etch rather than polish.

The time for etching and cleaning is reduced from 26 minutes to less than 100 seconds and the dental casting metal when removed, is clean and ready for use after rinsing. The actual prior art total time consumed in preparation is 35 minutes when the additional 9 minutes normally required for another setup and visit are considered. This additional set-up time is entirely eliminated. The result is at least a two-fold and possibly as high as a tenfold increase in productivity of the dentist.

Although a preferred embodiment has been presented for illustrative purposes, there are a number of possible variations which can be substituted by those skilled in the art, once the broad principles of the invention have been explained, but which nevertheless remain within the scope of the invention. For example, a number of acids may be substituted for those cited in the preferred embodiment and they include phosphoric, citric, and perchloric acids. Although a separate cleaning and etching acid are preferred a single acid may be used for both functions.

The concentrations of the acids may also vary. For example, the sulfuric acid concentration in the etching solution of the preferred embodiment may vary five to fifty percent, while the hydrochloric concentration in the cleaner may vary from ten to thirty percent. Similarly, the nitric acid concentration in the etching solution may vary from 2 to 8 percent.

The casting metals may vary from those which do not contain gold to those which have only a low value of gold concentration and from those which do not contain silver to those which contain only a low value of silver. Typical dental casting metals include nickel-chromium-beryllium, nickel-chromium, chromium-cobalt, silver-palladium, high palladium (no silver).

Having described my invention, I claim:

1. A system for accelerating the etching and cleaning of metal castings used in dental restoration, comprising the steps of:
   (a) combining a liquid etchant and a cleaner to form a single bath for the metal to be cleaned and etched,
   (b) providing a first and a second electrode for immersion in the bath, the electrodes being electrically conductive, but resistant to etching and cleaning effects of the bath,
   (c) providing a direct current power supply, the positive potential output of the supply being connected to the first electrode while the negative potential output is connected to the second electrode, said direct current power supply limiting the current flow to less than 0.8 amperes per square centimeter of surface to be etched,
   (d) connecting the dental casting to the first electrode, the connection making electrical contact from the supply to the casting by way of the first electrode,
   (e) immersing the electrodes in the bath in separated positions which permit electrical current flow through the electrodes and the bath, the immersing of the electrodes places the metal casting in the bath, and
   (f) applying ultrasonic vibrations to the bath, the vibrations being transmitted through the bath to the metal casting to accelerate the etching and cleaning action.

2. A method as described in claim 1, wherein: the etchant is sulfuric acid and the cleaner is hydrochloric acid.

3. The method as described in claim 1, wherein:
   (a) the etchant is nitric acid, and
   (b) the cleaner is hydrochloric acid.

4. The method as claimed in claim 2, wherein the range of concentration of the sulfuric acid is five to fifty percent and the range of concentration of the hydrochloric acid is from 10 to 30 percent.

5. The method as described in claim 3, wherein:
   (a) the range of concentration of the nitric acid is from 2 to 8 percent, and
   (b) the range of concentration of the hydrochloric acid is 10 to 30 percent.

6. The method as claimed in claim 1, wherein the casting metals are selected from the group comprising of nongold containing alloys and low gold containing alloys.

7. The method of claimed in claim 1, wherein the casting metals are selected from the group comprising nickel-chromium-beryllium, nickel-chromium, chromium-cobalt, silver-palladium and palladium.

8. Apparatus for accelerating the etching and cleaning of metal castings used in dental restoration, comprising:
   (a) a noncorroding tank means, (b) a mixture of a liquid etchant and a cleaner to form a single bath for the metal to be cleaned and etched, said mixture being placed in said tank means,
(c) a first and a second electrode immersed in the bath, the electrodes being electrically conductive, but resistant to etching and cleaning effects of the bath,
(d) a direct current power supply, the positive potential output of the supply being connected to the first electrode while the negative potential output is connected to the second electrode,
(e) means for connecting the dental casting to the first electrode, the connection making electrical contact from the supply to the casting by way of the first electrode,
(f) means for immersing the electrodes in the bath in separated positions which permit electrical current flow through the electrodes and the bath, the immersing of the electrodes placing the metal casting in the bath,
(g) means for limiting the current from the power supply to maintain a current density of less than 0.8 amperes per square centimeter of surface to be etched, and
(h) means for applying ultrasonic vibrations to the bath, said means being positioned in contact with said bath to conduct the vibrations through the bath to the metal casting to accelerate the etching and cleaning action.

* * * * *